(12) United States Patent
You et al.

(10) Patent No.: US 8,501,803 B2
(45) Date of Patent: Aug. 6, 2013

(54) GARCINIA DERIVATIVE, ITS PREPARING METHOD AND MEDICINAL USE

(75) Inventors: Qidong You, Nanjing (CN); Xiaojian Wang, Nanjing (CN); Qian Yang, Nanjing (CN); Na Lu, Nanjing (CN); Changjun Lin, Nanjing (CN); Qinglong Guo, Nanjing (CN)

(73) Assignee: China Pharmaceutical University, Jiangsu (CN)

( * ) Notice: Subject to any disclaimer, the term of this patent is extended or adjusted under 35 U.S.C. 154(b) by 0 days.

(21) Appl. No.: 13/255,046

(22) PCT Filed: Nov. 9, 2010

(86) PCT No.: PCT/CN2010/078555
§ 371 (c)(1),
(2), (4) Date: Sep. 6, 2011

(87) PCT Pub. No.: WO2011/120303
PCT Pub. Date: Oct. 6, 2011

(65) Prior Publication Data
US 2012/0059050 A1    Mar. 8, 2012

(30) Foreign Application Priority Data

Apr. 2, 2010   (CN) .......................... 2010 1 0139385

(51) Int. Cl.
*A61K 31/335*   (2006.01)
*C07D 313/00*   (2006.01)

(52) U.S. Cl.
USPC .......................................... 514/450; 549/354

(58) Field of Classification Search
USPC .......................................... 514/450; 549/354
See application file for complete search history.

(56) References Cited

FOREIGN PATENT DOCUMENTS
WO   WO 2008/057604    *   5/2008
WO   WO 2008/057604 A2    5/2008

OTHER PUBLICATIONS

International Search Report dated Feb. 24, 2011, for corresponding International Patent Application No. PCT/CN2010/078555, 3 pages.
Lin, et al., "Progress in Total Synthesis of Novel Bridged *Garcinia* Nature Products", Chinese Journal of Organic Chemistry, 2008, vol. 28, No. 2, pp. 218-227.
Feng, et al., "Anti-tumor QSAR of gambogic acid analogues", Journal of China Pharmaceutical University, 2007, vol. 38, No. 4, pp. 311-314.
Mahabusarakam, et al., "Xanthone derivatives from *Cratoxylum cochinchinense* roots", Phytochemistry, 2006, vol. 67, pp. 470-474.
Shu-Geng, et al., "Novel Cytotoxic Polyprenylated Xanthonoids from *Garcinia gaudichaudii* (Guttiferae)", Tetrahedron, 1998, vol. 54, pp. 10915-10924.

* cited by examiner

*Primary Examiner* — Noble Jarrell
*Assistant Examiner* — Valerie Rodriguez-Garcia
(74) *Attorney, Agent, or Firm* — Christie, Parker & Hale, LLP

(57) ABSTRACT

The present invention relates to a field of pharmaceutical chemistry, more specifically, the present invention relates to a garcinia derivative Formula (I), its preparing method, and medicinal use. Wherein the definitions of $R_1$ and $R_2$ are disclosed in the specification of the present invention, and the derivative of the present invention is a structurally simplified analogue of the gambogic acid compound; wherein the gambogic acid compound possesses anti-cancer characteristics, and could be used for preparation of anti-tumor drugs.

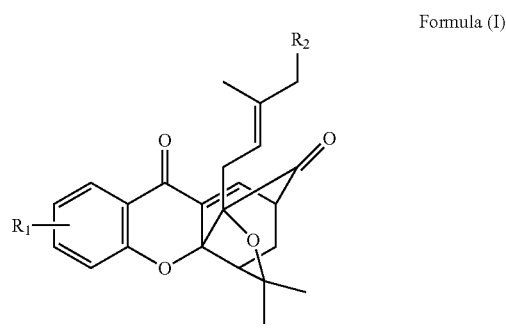

Formula (I)

7 Claims, No Drawings

GARCINIA DERIVATIVE, ITS PREPARING METHOD AND MEDICINAL USE

CROSS-REFERENCE TO RELATED APPLICATION(S)

This application is a National Phase Patent Application and claims the priority to and benefit of International Application Number PCT/CN2010/078555, filed on Nov. 9, 2010, which claims priority of Chinese Patent Application Number 201010139385.1, filed on Apr. 2, 2010.

FIELD OF THE INVENTION

The present invention relates to a field of pharmaceutical chemistry, more specifically, the present invention relates to a garcinia derivative, its preparing method, and medicinal use. The derivative of the present invention is a structurally simplified analogue of the gambogic acid compound which possesses anti-cancer characteristics and could be used for the preparation of anti-tumor drugs.

BACKGROUND OF THE INVENTION

It has been recently discovered that the natural product gambogic acid that is extracted from the gambogic resin of the Garcinia plant, is an effective ingredient in terms of anti-tumor characteristics. Research has shown that gambogic acid could selectively kill the various tumor cells without influencing the human hematopoietic or immune system. The gambogic acid could also combine with various proteins which are related to tumor formation and invasion, and thus induce apoptosis of the tumor cells. Therefore the gambogic acid could be used as an effective apoptosis inducer for various tumor systems. The formula of gambogic acid is shown below:

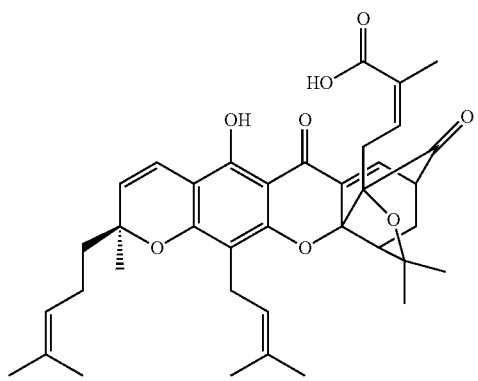

Formula of Gambogic Acid

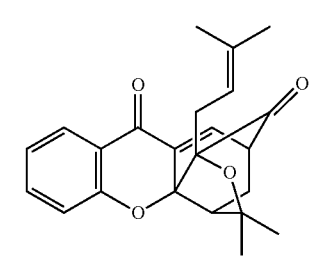

Compound (II)

Due to the fact that the molecular weight of gambogic acid is relatively high, the presence of a corresponding group in modified structure might lead to undesired druggability, furthermore, the gambogic acid is obtained from natural products via extraction and separation, which does not facilitate industrial production. A structurally simplified analogue of the gambogic acid has been reported (Compound (II)), however, the anti-pharmaceutical test of the structurally simplified analogue of the gambogic acid (Compound (II)) showed that its anti-tumor activity is significantly reduced compared to the gambogic acid, thereby leading to poor medicinal properties. (Bioorganic & Medicinal Chemistry 16 (2008) pgs. 4233-4241).

SUMMARY OF THE INVENTION

In the present invention, the structurally simplified analogue which is based on the gambogic acid caged scaffold structure, is prepared for the first time by using a tactic of precursor compound structural simplification. The compound of the present invention possesses similar anti-tumor activity when compared with that of gambogic acid, and it could be used for the preparation of anti-tumor drugs.

The compound structure of the present invention is shown in Formula (I):

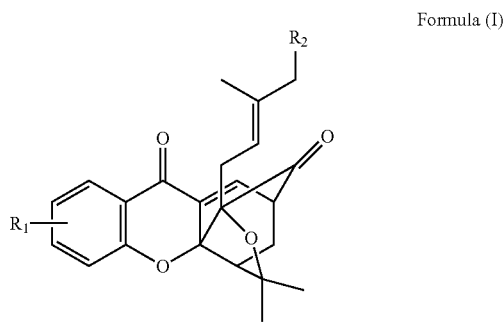

Formula (I)

Wherein $R_1$ is a single substituted group or a multi substituted group; when it is the single substituted group, $R_1$ is a hydroxyl group; and when it is the multi substituted group, one of the substituted groups is a hydroxyl group, the rest of substituted groups are selected from an amino group, a hydroxyl group, a nitro group, cyano group, an alkyl group containing $C_1$-$C_6$ carbons, or an alkenyl group containing $C_2$-$C_6$ carbons. More specifically, $R_1$ is at least one hydroxyl group, which can be only substituted by a hydroxyl group, or can be substituted by a hydroxyl group while the other substituted group is selected from one or several said substituted groups. Experiments show that the series compound of Formula (I), wherein $R_1$ is at least one hydroxyl group, has higher compound activity compared to Compound (II).

$R_2$ is hydrogen, halogen, a hydroxyl group, an alkoxy group containing $C_1$-$C_4$ carbons, an amide group containing $C_1$-$C_4$ carbons, a carboxyl group, or an aldehyde group.

The preferred $R_1$ is a single substituted group, and the preferred substituent is a hydroxyl group.

The preferred $R_1$ is a double substituted group, wherein one preferred substituent is a hydroxyl group and another preferred substituent is an isopentene group.

The preferred $R_2$ is hydrogen, a hydroxyl group, an aldehyde group, a carboxyl group, or an amide group.

The compound of the present invention is prepared via the following methods, wherein the reaction formula is:

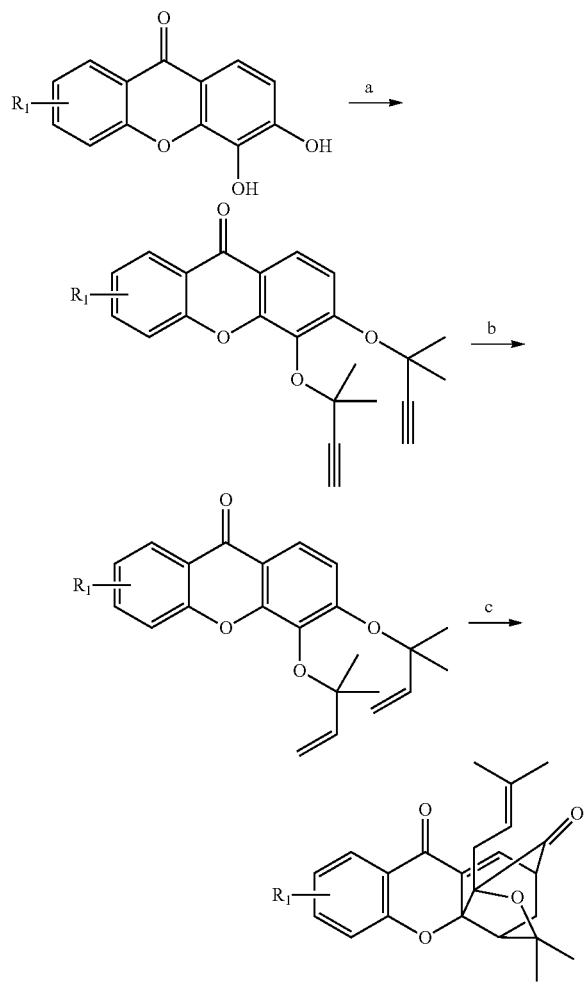

Wherein the included reagents and conditions are as follows: a. $K_2CO_3$, KI, chloro-methyl-butyne, CuI and acetone; b. 10% Pd/$BaSO_4$, ethyl acetate; and c. DMF (N,N-dimethyl formamide).

Take the compound wherein $R_1$ is a hydroxyl group and $R_2$ is a hydrogen as an example, the said compound could be used as reference for the other substituent, the more detailed and preferred preparing method is shown as below:

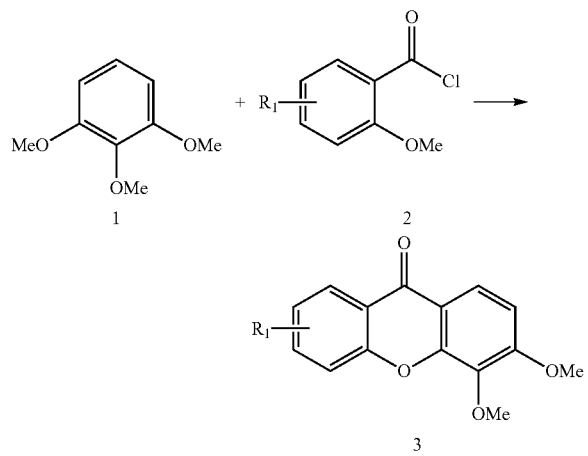

The compound 3 is obtained from compound 1 and compound 2 via a two-step reaction. The compound 1 and compound 2 react for 12-18 hours at room temperature. The preferred solvent is ethylether and $AlCl_3$ is added to the reaction solution. After the reaction, the obtained product without any treatment is directly heated to reflux and is then reacted for 20-30 hours in the strong alkali. As a result, the compound 3 is obtained. The preferred solvents are water and methanol; the ratio between said water and methanol is 1:1 to 4:1; and inorganic alkali, for instance, NaOH, KOH, and the like is then added to the reaction solution.

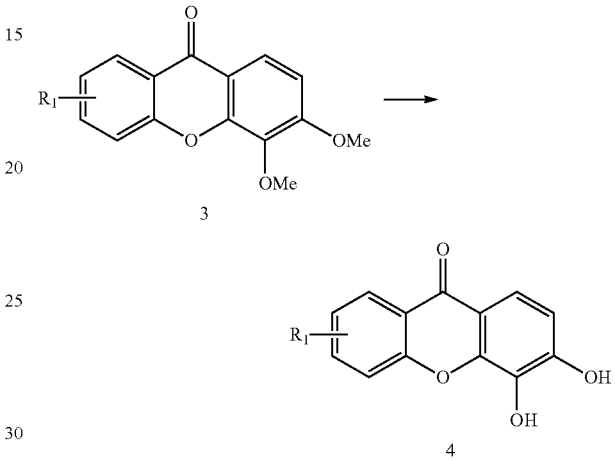

The compound 3 is heated and refluxed for 6 hours in a mixed solution containing 40% HBr and glacial acetic acid, as a result, the compound 4 is obtained. The solvent ratio between glacial acetic acid: 40% HBr is 1:1 to 4:1.

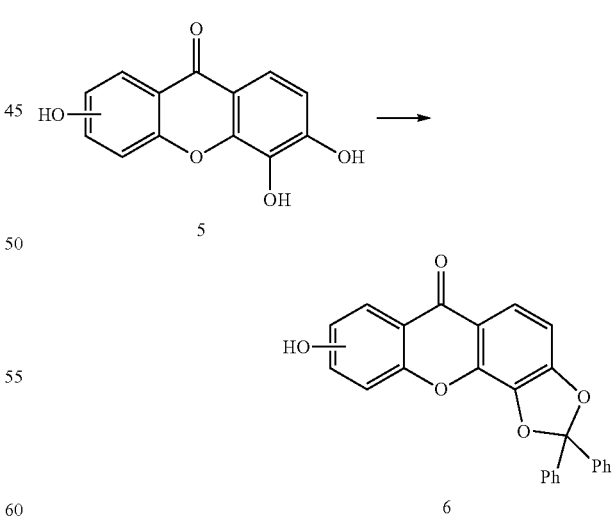

When $R_1$ is hydroxyl group, the compound 6 is obtained via reaction between the compound 5 and diphenyl dichloromethane, wherein the preferred solvent is xylene or diphenylether and the preferred reaction temperature is 160° C.-180° C.

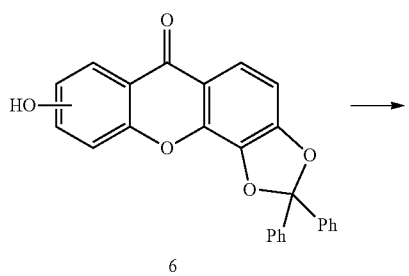

6

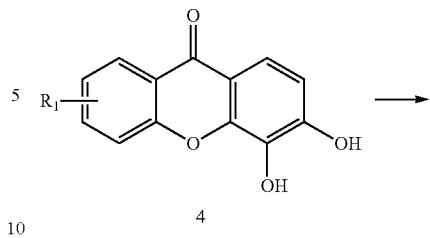

4

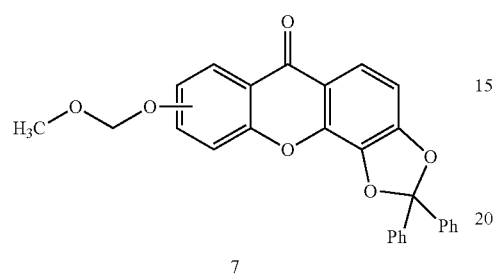

7

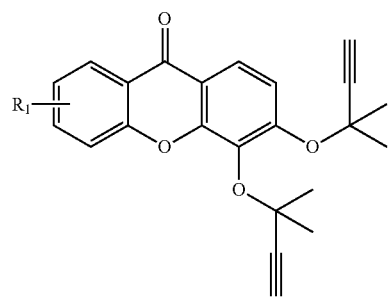

9

The compound 6 reacts with chloromethyl methyl ether at room temperature, and as a result, the compound 7 is obtained. The solvent is selected from acetonitrile, N,N-dimethyl formamide (DMF), acetone, dichloromethane, and the like; the reaction time is 6-10 hours; and the inorganic alkali or organic alkali, for instance, NaOH, KOH, $K_2CO_3$, triethylamine, and the like could be added during the reaction.

When $R_1$ is the other substituent or chloromethyl methyl, except said hydroxyl group, the compound 9 is obtained via reaction between the compound 4 and chloro-methyl-butyne, wherein the reaction temperature is 60° C.-90° C., and the solvent is selected from DMF, acetone, acetonitrile, dichloromethane, trichloromethane, and the like. The inorganic alkali or organic alkali, for instance, NaOH, KOH, $K_2CO_3$, triethylamine, and the like should also be added to the reaction, furthermore, the catalyst CuCl, CuI, or KI should also be added.

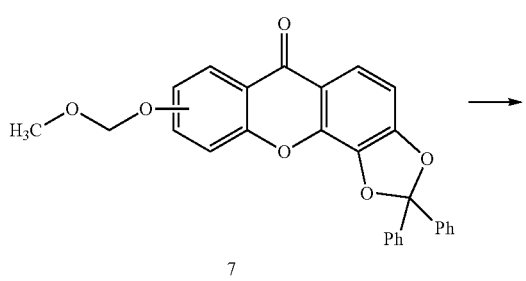

7

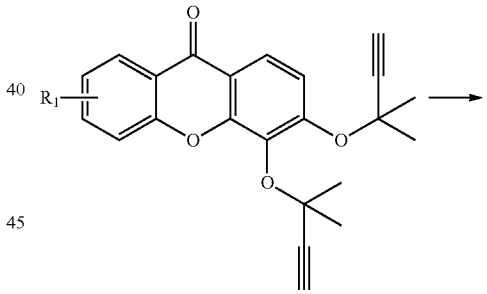

9

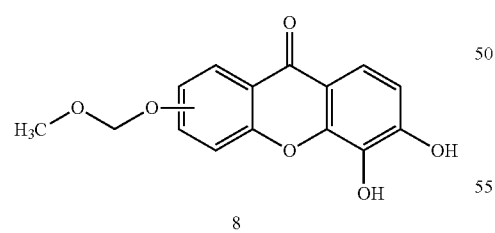

8

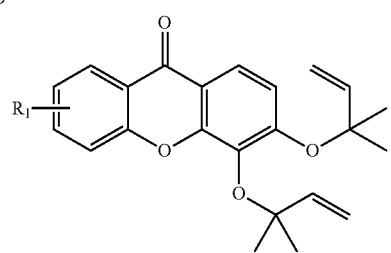

10

The compound 8 is obtained via hydrogenation of the compound 7 at normal pressure, wherein the reaction temperature is 20° C.-50° C.; the solvent is selected from THF, acetonitrile, DMF, methanol, trichloromethane, and the like; and a hydrogenation catalyst should also be added, for instance, 5% Pd/C, 10% Pd/C, and the like.

The compound 10 is formed via hydrogenation of the compound 9 at normal pressure, wherein the reaction temperature is 20° C.-50° C.; the solvent is selected from ethyl acetate, THF, acetonitrile, ethanol, and the like; a hydrogenation catalyst, for instance, 5% Pd/C, 10% Pd/C, 5% Pd—$BaSO_4$, 10% Pd—$BaSO_4$, and the like, should also be added.

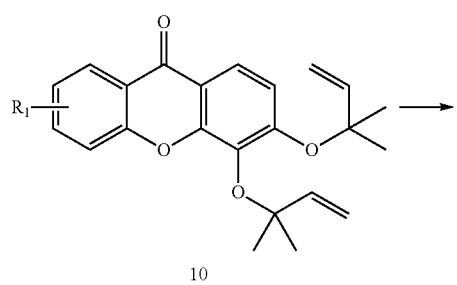

10

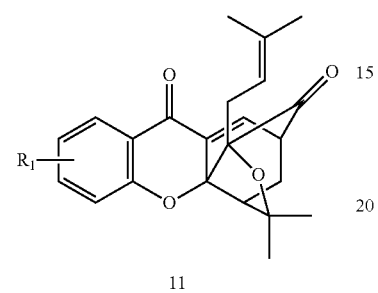

11

The compound 10 is heated to be rearranged, and as a result, the compound 11 is obtained, wherein the reaction temperature is 120° C.-180° C., and the solvent is selected from toluene, DMF, diphenyl ether, and the like.

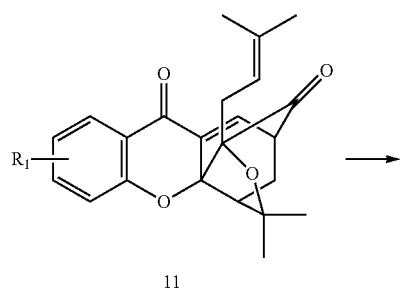

11

The compound 12 is obtained via oxidation of the compound 11, wherein the reaction temperature is 25° C.-40° C., and the preferred oxidants are $SnO_2$ and t-butyl hydroperoxide, lead tetraacetate, and the like. The solvent is selected from toluene, dichloromethane, trichloromethane, DMF, and the like.

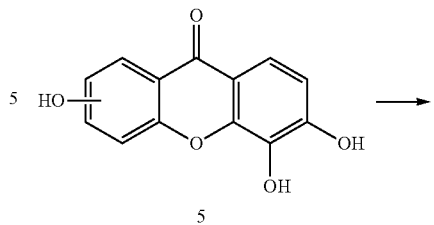

5

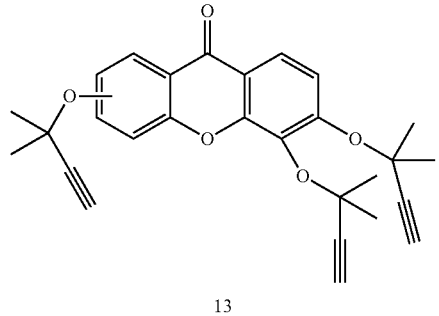

13

When $R_1$ is double substituted by a hydroxyl group and an isopentene group, the compound 5 reacts with chloro-methyl-butyne, and as a result, the compound 13 is obtained, wherein the reaction temperature is 60° C.-90° C., and the solvent is selected from DMF, acetone, acetonitrile, dichloromethane, trichloromethane, and the like. An inorganic alkali or organic alkali, for instance, NaOH, KOH, $K_2CO_3$, or triethylamine should be added to the reaction, and CuCl, CuI, or KI should also be added as catalyst.

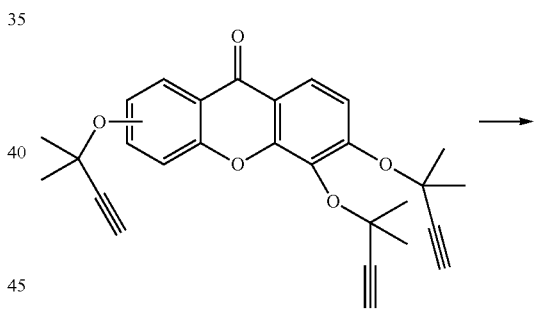

13

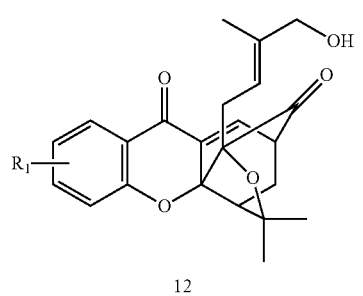

12

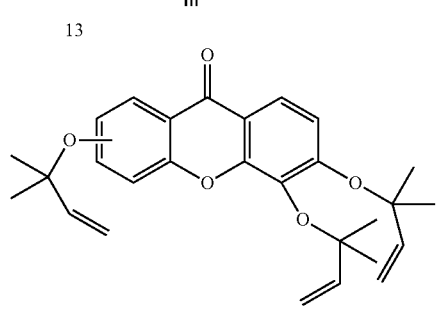

14

The compound 14 is obtained via hydrogenation of the compound 13 at normal pressure, wherein the reaction temperature is 20° C.-50° C.; the solvent is selected from ethyl acetate, THF, acetonitrile, ethanol, and the like; and a hydrogenation catalyst, for instance, 5% Pd/C, 10% Pd/C, 5% Pd—$BaSO_4$, 10% Pd—$BaSO_4$, and the like should also be added.

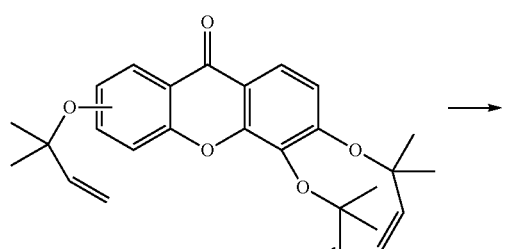

14

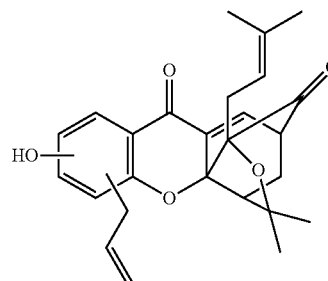

15

The compound 14 is heated to be rearranged, as a result, the compound 15 is obtained, wherein the reaction temperature is 120° C.-180° C., and the solvent is selected from toluene, DMF, diphenyl ether, and the like.

The compound of Formula (I) is purified by a common separation method, for instance, recrystallization, column chromatography, and the like.

The present invention also includes a hydrate, a stereomer, and/or a solvate of compound of Formula (I).

A pharmaceutically acceptable carrier, for instance, a tablet, a capsule, a powder, a syrup, a liquid, a suspension, or an injection could be a carrier for the compound of the present invention so as to form normal pharmaceutical preparations, and furthermore, the normal pharmaceutic adjuvants, for instance, a flavor, a sweetening agent, a liquid or solid filler, or a thinner, could also be included in the carrier for the compound of the present invention.

The compound of the present invention could be served as an oral or injection manner in the clinical administration.

The clinical dosage of the compound of present invention is 0.01 mg/day to 1000 mg/day, furthermore, according to the health conditions and dosage types, the clinical dosage which may deviate from said range could also be accepted.

The results obtained from the pharmaceutical test show that the compound of the present invention has relatively strong anti-proliferative activity with the tumor cells, which is comparable with that of natural gambogic acid. Therefore, the compound of the present invention might be an attractive ingredient for use in the development of anti-tumor drugs.

The results obtained from the pharmaceutical test by using partial compounds of the present invention are as shown below:

Test method: The cells of log phase are cultivated in the culture plate with 96 pores, and each pore contains 100 μL of solution (including 1000-1200 tumor cells). The next day, different concentrations of the present compound are added to the treatment groups, each compound contains 4 to 5 dosage groups, and each dosage group contains at least 3 parallel pores. The solvent with an equivalent volume of the said compound is added to the control groups. The said culture plate is then placed in a 5% $CO_2$ incubator, cultured at 37° C., and the culture solution is discharged 4 days later. Next, 200 μL of the 0.2% MTT solution (RPMI1640 preparation) is added to each pore and incubated at 37° C. for 4 hours; the obtained supernatant is discharged; and 150 μL of DMSO is added to each pore so as to dissolve formazane particles. After slightly shaking the mixture, the optical density (OD) is measured by the ELIASA in the conditions of a resulting reference wavelength 450 nm and a detection wavelength 570 nm. The tumor cells treated with solvent are used as control groups, and the inhibition rate of the drugs against the tumor cells and IC50 are calculated according to the following equation. The obtained results are shown in Table 1 which displays the antiproliferative activity of the tumor cells $IC_{50}$ of the compound. The MCF-7 cells are human breast cancer cells and the BGC-823 cells are human gastric carcinoma cells.

$$\text{Inhibition rate} = \frac{\text{Average OD of comparison group} - \text{Average OD of treatment group}}{\text{Average OD of comparison group}} \times 100\%$$

TABLE 1

Antiproliferative activity of the tumor cells $IC_{50}$ of the compound.

| Compound No. | Corresponding Examples | MCF-7 cell $IC_{50}$ (μM) | BGC-823 cell $IC_{50}$ (μM) |
| --- | --- | --- | --- |
| CPUY I-1 | Example 1 | 9.16 | 3.59 |
| CPUY I-2 | Example 4 | 12.40 | 17.60 |
| CPUY I-5 | Example 10 | 5.79 | 15.00 |
| CPUY I-6 | Example 11 | 11.90 | 21.70 |
| CPUY I-7 | Example 12 | 10.90 | 18.20 |
| CPUY I-8 | Example 13 | 9.06 | 11.30 |
| II | | 13.90 | 20.30 |
| Gambogic acid | | 2.19 | 2.35 |

The present invention possesses the following advantages: the natural product of gambogic acid is not necessary to be used as raw material, instead the structurally simplified analogue of the gambogic acid (Formula (1)) can be directly prepared; the obtained structure is simple in comparison with that of the gambogic acid; the anti-tumor activity is the same as that of gambogic acid; and the obtained anti-tumor activity that resulted from the hydroxyl substitution is higher than that of the reported Compound (II).

DETAILED DESCRIPTION OF THE PREFERRED EMBODIMENTS

Example 1

The following formula represents a 3,3a,4,5-tetrahydro-3,3-dimethyl-1-(3-methyl-2-butenyl)-8-hydroxyl-1,5-dimethylene-1H,7H-furan[3,4-d]xanthene-7,13-diketone endocyclic compound (CPUY I-1).

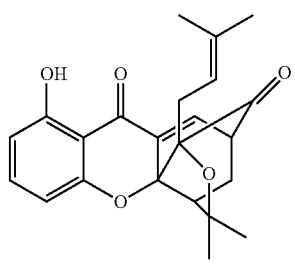 [SMILES: CC(C)=CCC12OC(C)(C)C3CC(C=C4C(=O)c5c(O)cccc5OC431)C2=O]

(1) Preparation of 1,5,6-trimethoxy-9H-xanthenone

In preparation of 1,5,6-trimethoxy-9H-xanthenone, 9.6 g (52.8 mmol) of 2,6-dimethoxy benzoic acid is dissolved in 140 mL of dried benzene, 24 mL of oxalyl chloride is added and mixed at room temperature for 24 hours. Subsequently, the solvent and remaining oxalyl chloride are removed via vacuum distillation; 160 mL of dried ethyl ether is added to dissolve the remains; 8.8 g (52.4 mmol) of 1,2,3-trimethoxybenzene is added; the mixture is stirred for 30 minutes in an ice-bath; 20 g (152 mmol) of anhydrate $AlCl_3$ is added and reacted at room temperature for 20 hours; the over amount of $AlCl_3$ is quenched with the diluted HCl solution (15%) and then extracted with ethyl acetate (2×100 mL); the organic phase is dried with anhydrous sodium sulfate and condensed; and as a result, 16 g of yellow solid is obtained. The obtained solid is directly dispersed in 240 mL of mixed solution containing methanol and water (methanol: water=5:3) without purification; 23.2 g (58.36 mmol) of NaOH is added; the mixture is stirred and refluxed at 110° C. for 36 hours; 6 mol/L of HCl is added until the pH value is adjusted to 6-8; and as a result, a large amount of solid is precipitated. The said precipitation is filtered, and the resulting filter cake is purified with the aid of column chromatography, wherein the eluent is the mixed solution containing petroleum ether and ethyl acetate (petroleum ether:ethyl acetate=4:1), and as a result, 12.8 g white solid is obtained, and the productivity is 85%; m.p. is 144.6° C.-145.7° C.; 1H-NMR (300 MHz, CD3COCD3): 3.95 (m, 6H), 4.01 (s, 3H), 6.97 (d, 1H, J1=8.4 Hz, J2=0.6 Hz), 7.14 (d, 1H, J1=8.4 Hz, J2=0.6 Hz), 7.15 (d, 1H, J=9.0 Hz), 7.69 (t, 1H, J=8.4 Hz), 7.89 (d, 1H, J=9 Hz); EI-MS (m/z): 286 (M+).

(2) Preparation of 1,5,6-trihydroxy-9H-xanthenone

In preparation of 1,5,6-trihydroxy-9H-xanthenone, 15 g (52.5 mmol) of 1,5,6-trimethoxy-9H-xanthenone is dissolved in 500 mL of mixed solution (HBr:acetic acid=1:2), the said mixture is heated to 120° C., and refluxed for 12 hours. Next, 10% NaOH solution is added until the pH value is adjusted to 3-4, and as a result, a large amount of gray solid is precipitated. The said precipitation is filtered, and as a result, 9 g of grey solid is obtained, and the productivity is 70%; m.p. is 300° C.-301° C.; $^1$H-NMR (300 MHz, DMSO-d6): 6.77 (dd, 1H, J1=8.3 Hz, J2=0.87 Hz,), 6.97 (d, 1H, J=8.8 Hz), 67.05 (dd, 1H, J1=8.3 Hz, J2=0.87 Hz), 7.57 (d, 1H, J=8.8 Hz), 7.68 (t, 1H, J=8.3 Hz), 9.53 (s, 1H), 10.68 (s, 1H), 12.91 (s, 1H); ESI-MS (m/z): 243 ([M−H]−).

(3) Preparation of 7-hydroxy-2,2-diphenyl-6H-[1,3]dioxolo[4,5-c]-6-xanthenone

In preparation of 7-hydroxy-2,2-diphenyl-6H-[1,3]dioxolo[4,5-c]-6-xanthenone, 5 g (22.3 mmol) of 1,5,6-trihydroxy-9H-xanthenone is added to 40 mL of diphenyl ether, subsequently, 7 mL (35 mmol) of diphenyl dichloromethane is added, and the mixture reacts at 175° C. for 4 hours. After the reaction solution is cooled, 800 mL petroleum ether is added, and as a result, a large amount of gray solid is precipitated. The said precipitation is filtered and purified with the aid of column chromatography, wherein the eluent is the mixed solution containing petroleum ether and ethyl acetate (petroleum ether:ethyl acetate=8:1), and as a result, 6.1 g of light yellow solid is obtained, and the yield is 79%; m.p. is 203° C.-205° C.; 1H-NMR (300 MHz, CDCl3): 6.72 (d, J=8.4 Hz, 1H), 6.90 (d, J=9.3 Hz, 1H), 6.93 (d, J=9.3 Hz, 1H), 7.34 (m, 6H), 7.49 (t, J=9.3 Hz, 1H), 7.57 (m, 4H), 7.82 (d, J=8.4 Hz, 1H), 12.70 (s, 1H); EI-MS (m/z): 408.

(4) Preparation of 7-methoxy methylenedioxy-2,2-diphenyl-6H-[1,3]dioxolo[4,5-c]xanthenone In preparation of 7-methoxy methylenedioxy-2,2-diphenyl-6H-[1,3]-dioxolo[4,5-c]xanthenone, 6.1 g (14.85 mmol) of 7-hydroxy-2,2-diphenyl-6-[1,3]dioxolo[4,5-c]-6-xanthenone is dissolved in 200 mL of acetone, 1.2 g (29.7 mmol) of NaH is added, the mixture is mixed at 0° C. for 0.5 hours, 2.43 mL (29.7 mmol) chloromethyl methyl ether is added, and at the end of addition, the mixture reacts at room temperature for 8 hours. The reaction solution is then poured into 800 mL of ice water, and as a result, a large amount of white solid is precipitated. The said precipitation is filtered and dried, and as a result, 6 g of white solid is obtained, and the yield is 90%; m.p. is 138° C.-140° C.; 1H-NMR (300 MHz, CDCl3): 3.56 (s, 3H), 5.36 (s, 2H), 6.94 (d, J=8.4 Hz, 1H), 7.04 (dd, 1H, J1=8.2 Hz, J2=0.6 Hz, 1H), 7.17 (dd, J=8.2 Hz, J2=0.6 Hz, 1H), 7.40 (m, 6H), 7.55 (dd, J=8.2H, J2=0.6 Hz), 7.64 (m, 4H), 7.89 (d, J=8.4 Hz, 1H); EI-MS (m/z): 452 (M+).

(5) Preparation of 3,4-dihydroxy-7-methoxy methylenedioxy-9H-xanthenone

In preparation of 3,4-dihydroxy-7-methoxy methylenedioxy-9H-xanthenone, 6 g (13.2 mmol) of 7-methoxy methylenedioxy-2,2-diphenyl-6H-[1,3]-dioxolo[4,5-c]xanthenone is dissolved in 420 ml of mixed solution containing methanol: THF=1:1, 700 mg of 10% Pd/C is added, and the mixture undergoes hydrogenation at normal pressure for 24 hours. The reaction solution is filtered, the filtrate is condensed, the residue is purified with the aid of column chromatography (petroleum ether/ethyl acetate=1:1), and as a result, 3 g of dark green solid is obtained, and the yield is 78.5%; m.p. is greater than 300° C.; 1H NMR (300 MHz, DMSO): 3.46 (s, 3H), 5.31 (s, 2H), 6.90 (d, 1H, J=8.25 Hz), 7.02 (dd, 1H, J1=8.8 Hz, J2=2.2 Hz), 7.14 (dd, J1=8.8 Hz, J2=2.2 Hz), 7.84 (dd, 1H, J1=8.8 Hz, J2=2.2 Hz), 8.25 (d, 1H, J=8.25 Hz); EI-MS (m/z) 288 (M+), 288, 256, 244.

(6) Preparation of 1-hydroxy-5,6-dimethyl butynyloxy-9H-xanthenone

In preparation of 1-hydroxy-5,6-dimethyl butynyloxy-9H-xanthenone, 3 g (10.2 mmol) of 3,4-dihydroxy-7-methoxy methylenedioxy-9H-xanthenone is dissolved in 200 mL of acetonitrile, and subsequently, KI (1.73 g, 10.2 mmol), 1,8-diazabicyclo-dicyclo(5,4,0)-7-undecene (7.2 mL, 57.12 mmol), and CuI (300 mg, 1.6 mmol) are added, respectively. The said mixture is stirred at room temperature for 10 minutes; is placed in an ice-bath; chloro-methyl-butyne (8.4 ml, 81.6 mmol) is added; and the said mixture then reacts at room temperature for 48 hours.

It is then vacuum distilled to condense acetonitrile; 800 mL of water and 200 mL of ethyl ether are added; and 2 mol/L of HCl are added until the pH value is adjusted to 3. The mixture is stirred at room temperature for 4 hours; the water phase is extracted with 800 mL of ethyl acetate four times; the extracted ethyl acetate is dried with anhydrous sodium sulfate; the organic phase is condensed; the resulting residue is purified with the aid of column chromatography, wherein the eluent is the mixed solution containing petroleum ether and ethyl acetate (petroleum ether:ethyl acetate=8:1); and as a result, 2 g of brown crystals are obtained, and the productivity is 49%; m.p. is 138° C.-140° C.; 1H-NMR (300 MHz, CDCl3): 1.79 (s, 6H), 1.83 (s, 6H), 2.28 (s, 1H), 2.66 (s, 1H), 6.79 (dd, J1=8.1 Hz, J2=0.6 Hz, 1H), 6.95 (dd, J1=8.1 Hz, J2=0.6 Hz, 1H), 7.56 (t, J=8.1 Hz, 1H), 7.66 (d, J=9 Hz, 1H), 7.98 (d, J=9 Hz, 1H), 12.71 (s, 1H); EI-MS (m/z): 376, 310, 244.

(7) Preparation of 1-hydroxy-5,6-dimethyl butenyl-9H-xanthenone

In preparation of 1-hydroxy-5,6-dimethyl butenyl-9H-xanthenone, 1-hydroxy-5,6-dimethyoxy butynyloxy-9H-xanthenone (2 g, 5.3 mmol) is dissolved in 18 mL of ethanol, 50 mg of 10% Pd/BaSO$_4$ is added, and the mixture undergoes hydrogenation at normal pressure for 12 hours. The obtained is filtered, the reaction solution is condensed, and the obtained gray solid is washed with petroleum ether and is used directly in the following step.

(8) Preparation of the 3,3a,4,5-tetrahydro-3,3-dimethyl-1-(3-methyl-2-butenyl)-8-hydroxy-1,5-dimethylene-1H,7H-furan[3,4-d]xanthene-7,13-diketone endocyclic compound In preparation of the 3,3a,4,5-tetrahydro-3,3-dimethyl-1-(3-methyl-2-butenyl)-8-hydroxy-1,5-dimethylene-1H,7H-furan[3,4-d]xanthene-7,13-diketone endocyclic compound, 1.8 g of 1-hydroxy-5,6-dimethyl butenyl-9H-xanthenone is dissolved in 15 mL of DMF and the said mixture reacts at 125° C. for 6 hours. The solvent is evaporated, the resulting residue is purified with the aid of column chromatography (petroleum ether/ethyl acetate=6:1), and as a result, 1.2 g brown solid is obtained, and the yield is 66%. The obtained solid is further crystallized in the mixed solution containing acetone and petroleum ether (acetone:petroleum ether=1:20), and the brown crystal is obtained, and the m.p. is 130° C.-132° C.; 1H-NMR (300 MHz, CDCl3): 0.95 (s, 3H), 1.18-1.25 (m, 4H), 1.30 (s, 3H), 1.61 (s, 3H), 2.26 (dd, J1=13.5 Hz, J2=4.5 Hz, 1H), 2.37 (d, J=9.6 Hz, 1H), 2.54 (d, J=7.8 Hz, 2H), 3.44 (dd, J1=6.9 Hz, J2=4.5 Hz, 1H), 4.34 (m, 1H), 6.43 (dd, J1=8.1 Hz, J2=0.9 Hz, 1H), 6.45 (dd, J1=8.1 Hz, J2=0.9 Hz, 1H), 7.32 (t, J=8.1 Hz, 1H), 7.41 (d, J=9.6 Hz, 1H), 12.00 (s, 1H).

Example 2

The following formula represents a 3,3a,4,5-tetrahydro-3,3-dimethyl-1-(3-methyl-2-butenyl)-8-hydroxyl-1,5-dimethylene-1H,7H-furan[3,4-d]xanthene-7,13-diketone endocyclic compound (CPUY I-1).

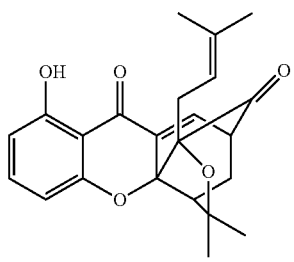 [SMILES: CC(C)=CCC12OC(C)(C)C3CC(C=C4C(=O)c5c(O)cccc5OC431)C2=O]

(1) Preparation of 5,6-dihydroxyl-1-acetoxy xanthenone

In preparation of 5,6-dihydroxyl-1-acetoxy xanthenone, 5 g (20.5 mmol) of 1,5,6-trihydroxy-9H-xanthenone is dissolved in 35 mL of DMF; subsequently, 5 g of K$_2$CO$_3$, 500 mg of KI, and 7 mL (61 mmol) of benzyl chloride are added; the said mixture reacts at 65° C. for 2 hours; the reaction solution is cooled and transferred to 2 mol/L of HCl; and as a result, a large amount of solid is precipitated. The said precipitation is vacuum filtered and dried, and as a result, 8 g of light yellow solid 5,6-dibenzyl-1-hydroxyl-xanthenone is obtained. The said obtained solid is directly dissolved in 80 mL of dichloromethane, subsequently, 5 g of DMAP and 6 mL of acetic anhydride are added in turn, and the said mixture reacts at a constant temperature of 25° C. for 2 hours. The obtained reaction solution is washed twice with saturated NH$_4$Cl solution (80 mL×2) and twice with water (80 mL×2); the obtained organic phase is dried with anhydrous sodium sulfate; and 8 g of white solid 5,6-dibenzyl-1-acetyl xanthenone is obtained via vacuum condensation. The said obtained solid is dissolved in 400 mL of mixed solution containing THF and methanol (THF:methanol=1:1), and hydrogenation takes place under normal pressure with the aid of 10% Pd/C. The said mixture reacts at a constant temperature of 40° C. for 2 hours; the obtained substance is filtered; the filtrate is condensed; 200 mL of petroleum ether is added to wash the resulting residue; 4.5 g of grey solid is obtained via vacuum filtration; and the obtained solid is directly used in the following step without purification.

(2) Preparation of 5,6-dimethyl butynyl-1-acetoxy xanthenone

In preparation of 5,6-dimethyl butynyl-1-acetoxy xanthenone, 5,6-dihydroxy-1-acetoxy xanthenone (5 g, 17.5 mmol) is dissolved in 80 mL of acetone, and 5 g of K$_2$CO$_3$, 5 g of KI, 1 g of CuI, and 7 mL of chloro-methyl-butyne are added in turn. The said mixture is heated and refluxed for 5 hours. At the end of the reaction, 300 mL of water and 80 mL of ethyl acetate are added and mixed; and the organic phase is separated and dried with anhydrous sodium sulfate. The obtained is separated with the aid of column chromatography (petroleum ether: ethyl acetate=8:1) and 3 g of yellow solid is obtained, and the yield is 41%; 1H-NMR (300 MHz, CDCl$_3$): 1.76 (s, 3H), 1.82 (s, 3H), 2.31 (s, 1H), 2.50 (s, 3H), 2.65 (s, 1H), 6.97 (d, J=7.5 Hz, 1H), 7.42 (d, J=8.4 Hz, 1H), 7.59-7.69 (m, 2H), 7.95 (s, J=9 Hz, 1H).

(3) Preparation of 5,6-dimethyl butenyl-1-acetoxy xanthenone

In preparation of 5,6-dimethyl butenyl-1-acetoxy xanthenone, 5,6-bis(dimethyl butynyl-1-acetoxy xanthenone (3 g, 12.3 mmol) is dissolved in 70 mL of mixed solution containing ethyl acetate and ethanol (ethyl acetate:ethanol=1:3), and undergoes hydrogenation at normal pressure with the aid of 300 mg 10% Pd—BaSO$_4$. The obtained reacts at room temperature for 16 hours; the reaction solution is filtered; and the solvent is condensed and dried in reduced pressure, and is used directly in the following step.

(4) 3,3a,4,5-tetrahydro-3,3-dimethyl-1-(3-methyl-2-butenyl)-8-acetoxy-1,5-dimethylene-1H,7H-furan[3,4-d]xanthene-7,13-diketone endocyclic compound In preparation of the above compound, 1-hydroxyl-5,6-dimethyl butenyl-9H-xanthenone (1.8 g, 7.3 mmol) is dissolved in 15 mL of DMF and the said mixture reacts at 125° C. for 6 hours and the solvent is evaporated. The resulting residue is separated with the aid of column chromatography (petroleum ether: ethyl acetate=6:1), and as a result, 1 g of yellow solid is obtained, and the yield is 55.6%; 1H-NMR (300 MHz, CDCl3): 0.99 (s, 3H), 1.18-1.25 (m, 4H), 1.30 (s, 3H), 1.61 (s, 3H), 2.26 (dd, J1=13.5 Hz, J2=4.5 Hz, 1H), 2.28 (s, 3H), 2.37 (d, J=9.6, 1H), 2.54 (d, J=7.8 Hz, 2H), 3.44 (dd, J1=6.9 Hz, J2=4.5 Hz, 1H), 4.34 (m, 1H), 6.43 (dd, J1=8.1 Hz, J2=0.9 Hz, 1H), 6.45 (dd, J1=8.1 Hz, J2=0.9 Hz, 1H), 7.32 (t, J=8.1 Hz, 1H), 7.41 (d, J=9.6 Hz, 1H).

(5) 3,3a,4,5-tetrahydro-3,3-dimethyl-1-(3-methyl-2-butenyl)-8-hydroxyl-1,5-dimethylene1H,7H-furan[3,4-d]xanthene-7,13-diketone endocyclic compound In preparation of the above compound, 3,3a,4,5-tetrahydro-3,3-dimethyl-1-(3-methyl-2-butenyl)-8-acetoxy-1,5-dimethylene-1 H,7H-furan[3,4-d]xanthene-7,13-diketone endocyclic compound (1 g, 4 mmol) is dissolved in 10 mL of mixed solution containing THF and methanol (THF:methanol=1:1), subsequently, 4 mL (4 mol/L) of HCl is added and the mixture is mixed at room temperature for 6 hours, 10 mL ethyl acetate and 10 mL 10% NaHCO$_3$ are added, and the obtained organic phase is separated and dried with anhydrous sodium sulfate. The obtained is separated with the aid of column chromatography (petroleum ether: ethyl acetate=4:1), and as a result, 810 mg of yellow solid is obtained, and the productivity is 90%; m.p. is 130° C.-132° C.; 1H-NMR (300 MHz, CDCl3): 0.95 (s, 3H), 1.18-1.25 (m, 4H), 1.30 (s, 3H), 1.61 (s, 3H), 2.26 (dd, J1=13.5 Hz, J2=4.5 Hz, 1H), 2.37 (d, J=9.6, 1H), 2.54 (d, J=7.8 Hz, 2H), 3.42 (dd, J1=6.9 Hz, J2=4.5 Hz, 1H), 4.33 (m, 1H), 6.43 (dd, J1=8.1 Hz, J2=0.9 Hz, 1H), 6.45 (dd, J1=8.1 Hz, J2=0.9 Hz, 1H), 7.32 (t, J=8.1 Hz, 1H), 7.41 (d, J=9.6 Hz, 1H), 12.00 (s, 1H).

Example 3

The following formula represents a (E)-3,3a,4,5-tetrahydro-3,3-dimethyl-1-(3-hydroxymethyl-2-butenyl)-8-hydroxy-1,5-dim ethylene-1H,7H-furan[3,4-d]xanthene-7,13-diketone endocyclic compound:

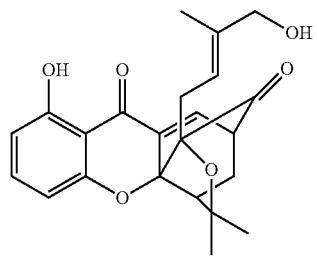 [SMILES: C/C(=C\CC12OC(C)(C)C3CC(C=C4C(=O)c5c(O)cccc5OC431)C2=O)CO]

(1) The synthetic method in preparation of 3,3a,4,5-tetrahydro-3,3-dimethyl-1-(3-methyl-2-butenyl)-8-hydroxy-1,5-dimethylene-1H,7H-furan[3,4-d]xanthene-7,13-diketone endocyclic compound is same as those described in Example 1 and Example 2.

(2) In preparation of (E)-3,3a,4,5-tetrahydro-3,3-dimethyl-1-(3-hydroxymethyl-2-butenyl)-8-hydroxyl-1,5-dimethylene-1H,7H-furan[3,4-d]xanthene-7,13-diketone endocyclic compound, 800 mg of 3,3a,4,5-tetrahydro-3,3-dimethyl-1-(3-methyl-2-butenyl)-8-hydroxy-1,5-dimethylene-1H,7H-furan[3,4-d]xanthene-7,13-diketone endocyclic compound is dissolved in 5 mL of dichloromethane, 80 mg of SnO$_2$ and 1 ml of t-butyl hydroperoxide are added, and the said mixture is stirred at room temperature for 24 hours. After the reaction, the obtained is washed with water three times, the organic phase is separated, and is then separated again with the aid of column chromatography (petroleum ether: ethyl acetate=2:1), and as a result, 780 mg of yellow solid is obtained, and the yield is 94%.

Example 4

The following formula represents a 3,3a,4,5-tetrahydro-3,3-dimethyl-1-(3-methyl-2-butenyl)-10-hydroxyl-1,5-dimethylene-1H,7H-furan[3,4-d]xanthene-7,13-diketone endocyclic compound (CPUY I-2).

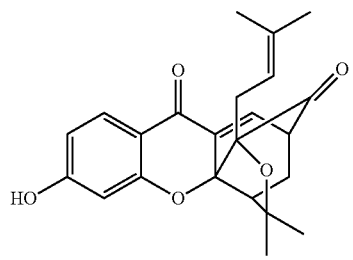 [SMILES: CC(C)=CCC12OC(C)(C)C3CC(C=C4C(=O)c5ccc(O)cc5OC431)C2=O]

(1) Preparation of 3-hydroxyl-4,6-dimethoxy-9H-xanthenone

In preparation of 3-hydroxyl-4,6-dimethoxy-9H-xanthenone, 2.4 g (13.14 mmol) of 2,4-dimethoxy benzoic acid is dissolved in 60 mL of dried dichloromethane, 5 mL of oxalyl chloride is added, and the said mixture is stirred at room temperature for 24 hours. Once the solvent is evaporated, 80 mL of ethyl ether is added to dissolve resulting residue; 2.19 g (13.03 mmol) of 1,2,3-trimethoxy benzene is added; the said mixture is cooled in an ice-bath for 30 min, 5.0 g of anhydrate AlCl$_3$ (37.5 mmol) is added; the said mixture reacts at room temperature for 12 hours; and the over amount of AlCl$_3$ is quenched with the aid of diluted HCl solution (15%).

The obtained is then extracted with ethyl acetate (80 mL×2) and dried with anhydrous sodium sulfate. The resulting residue is condensed in reduced pressure and is directly dissolved in the mixed solution containing methanol (20 mL) and 30% NaOH (40 mL). The said mixture is heated and refluxed for 14 hours, the pH value of the obtained solution is adjusted with the aid of 6 mol/L HCl until the pH value reaches 6, the said mixture is vacuum filtered and dried, and as a result, 3 g of crude product is obtained, and the yield is 81%; m.p. is 120.2° C.-121.2° C.; 1H-NMR (300 MHz, CD3COCD3): 3.98-4.03 (m, 9H), 7.00 (dd, 1H, J1=8.9 Hz, J2=2.4 Hz), 7.09 (d, 1H, J=2.4 Hz), 7.19 (d, 1H, J=9.0 Hz), 7.95 (d, 1H, J=9.0 Hz), 8.13 (d, 1H, J=8.9 Hz); EI-MS (m/z): 286 [M+], 271, 256, 241.

(2) Preparation of 3,4,6-trihydroxyl-9H-xanthenone

In preparation of 3,4,6-trihydroxyl-9H-xanthenone, 8 g (2.79 mmol) of 3-hydroxyl-4,6-dimethoxy-9H-xanthenone is dissolved in 160 mL of mixed solution containing HBr and acetic acid (HBr:acetic acid=1:2) (V: V), the said mixture is heated to 120° C. and refluxed for 12 hours, the pH value of the obtained mixture is adjusted with the aid of 10% NaOH solution until the pH value reaches 3-4, and as a result, a large amount of grey solid is precipitated. It is then vacuum filtered and purified with the aid of silica gel column chromatography (petroleum ether/ethyl acetate=1:1), and as a result, 5.8 g of grey solid is obtained, and the yield is 85%; m.p. is greater than 300° C. (reported m.p. is 340° C.-341° C.); 1H-NMR (300 MHz, DMSO-d6): 6.83-6.93 (m, 3H,), 7.50 (d, 1H, J=8.8 Hz), 8.00 (d, 1H, J=8.8 Hz), 9.28 (s, 1H), 10.31 (s, 1H), 10.77 (s, 1H), ESI-MS (m/z): 243 ([M−H]−).

(3) Preparation of 9-hydroxyl-2,2-diphenyl-6H-[1,3]dioxolo[4,5-c]xanthenone

In preparation of 9-hydroxyl-2,2-diphenyl-6H-[1,3]dioxolo[4,5-c]xanthenone, 5 g (21 mmol) of 3,4,6-trihydroxyl-9H-xanthenone is added to 30 mL of diphenyl ether, 7 mL (36 mmol) of diphenyl dichloromethane is added, and then the said mixture reacts at 175° C. for 2 hours. The obtained is cooled, 100 mL of petroleum ether is added, and as a result, a large amount of yellow solid is precipitated. The obtained solid is vacuum filtered and purified with the aid of filter cake column chromatography, the eluent (petroleum ether/ethyl acetate=4:1) is used, and as a result, 5.1 g of yellow solid is obtained, and the yield is 61%; m.p. is 231° C.-232° C.; 1H-NMR (300 MHz, CD3COCD3): 6.94-6.98 (m, 2H), 7.1 (d, 2H, J=8.7 Hz), 7.47~7.50 (m, 6H), 7.66-7.69 (m, 4H), 7.85 (d, J=8.7 Hz, 1H), 8.10 (q, J=9 Hz, 1H); EI-MS (m/z) 408 [M+], 331, 303, 165.

(4) Synthesis of 9-methoxy methyleneoxy-2,2-diphenyl-6H-[1,3]dioxolo[4,5-c]xanthenone In preparation of 9-methoxy methyleneoxy-2,2-diphenyl-6H-[1,3]dioxolo[4,5-c]xanthenone, 5 g (2.45 mmol) of 9-hydroxyl-2,2-diphenyl-6H-[1,3]dioxolo[4,5-c]xanthenone is dissolved in 70 mL of DM, 515 mg (4.29 mmol) of sodium hydride is added, and the said mixture is mixed for 10 min. Subsequently, 1.8 mL (23 mmol) of chloromethyl methyl ether is added; the said mixture reacts at room temperature for 8 hours; 200 mL water is added to the said reaction solution; the said solution is extracted with 200 mL of ethyl acetate four times; and the organic phase is condensed. The resulting residue is separated and purified with the aid of column chromatography (petroleum ether/ethyl acetate=4:1), and as a result, 5 g of white solid is obtained, and the yield is 99%; m.p. is 179° C.-181° C.; 1H NMR (300 MHz, CDCl3): 3.44 (s, 3H), 5.21 (s, 2H), 6.91-6.96 (m, 2H), 7.10 (s, J1=2.4 Hz, 1H), 7.32-7.36 (m, 6H), 7.54-7.59 (m, 4H), 7.82 (d, 1H, J=5.1 Hz), 8.17 (d, 1H, J=5.3 Hz); EI-MS (m/z) 452 (M+), 375, 331, 165, 105.

(5) Preparation of 3,4-dihydroxyl-6-methoxy methyleneoxy-9H-xanthenone

In preparation of 3,4-dihydroxyl-6-methoxy methyleneoxy-9H-xanthenone, 5 g (2.2 mmol) of 9-methoxy methyleneoxy-2,2-diphenyl-6H-[1,3]dioxolo[4,5-c]xanthenone is added to 90 ml of mixed solution containing ethanol and THF (ethanol: THF=1:1), 500 mg of 10% Pd/C is added, and the said mixture undergoes hydrogenation at normal pressure for 24 hours. The obtained reaction solution is vacuum filtered and the filtrate is condensed. The resulting residue is separated and purified with the aid of column chromatography (petroleum ether: ethyl acetate=2:1), and as a result, 5 g of light yellow solid is obtained, and the yield is 90%; m.p. is greater than 300° C.; 1H NMR (300 MHz, DMSO-d6): 3.52 (s, 3H), 5.30 (s, 2H), 6.97 (d, J=8.8 Hz, 1H), 7.04-7.07 (q, J1=2.2 Hz, J2=8.8 Hz, 1H), 7.14 (d, J=2.2 Hz, 1H), 7.84 (d, J=8.8 Hz, 1H), 8.25 (d, J=8.8 Hz, 1H); EI-MS (m/z) 288 (M+), 258, 215, 187, 167.

(6) Preparation of 3,4-dimethyl butynyl-6-methoxy methyleneoxy-9H-xanthenone

In preparation of 3,4-dimethyl butynyl-6-methoxy methyleneoxy-9H-xanthenone, 5 g (16.5 mmol) of xanthenone is dissolved in 80 mL of acetonitrile, and subsequently, 2.5 g (20 mmol) of KI, 9.5 mL of DBU, and 250 mg (0.028 mmol) of CuI are added in turn. Then 0.42 ml (3.3 mmol) of chloromethyl butyne is added; the said mixture reacts at room temperature for 24 hours; 800 mL water is added; the said mixture is stirred at room temperature for 15 min; the obtained water phase is extracted with 200 mL ethyl acetate four times; and the obtained organic phase is condensed. The resulting residue is separated and purified with the aid of column chromatography, the eluent (petroleum ether/ethyl acetate=8:1) is used, and as a result, 3.5 g of orange powder is obtained, and the yield is 45%; m.p. is 128° C.-130° C.; 1H-NMR (300 MHz, CDCl₃): 1.69 (s, 6H), 1.75 (s, 6H), 2.26 (s, 1H), 2.58 (s, 1H), 3.45 (s, 3H), 5.22 (s, 1H), 6.96 (d, J1=8.7 Hz, J2=2.1 Hz, 1H), 7.04 (d, J=2.1 Hz, 1H), 7.54 (d, J=9 Hz, 1H), 7.97 (s, J=9 Hz, 1H), 8.18 (d, J=8.7 Hz, 1H); EI-MS (m/z): 420, 405, 377, 354, 339, 324, 309, 295, 288, 244.

(7) Preparation of 2-methoxy methyleneoxy-5,6-dimethyl butenyl-9H-xanthenone

In preparation of 2-methoxy methyleneoxy-5,6-dimethyl butenyl-9H-xanthenone, 3.5 g of xanthenone is dissolved in 80 mL of ethanol, 350 mg of 10% Pd—BaSO₄ is added, and the said mixture undergoes hydrogenation at room temperature for 2 hours. The obtained reaction solution is vacuum filtered and the obtained filtrate is condensed. The resulting residue is separated and purified with the aid of column chromatography, the eluent (petroleum ether/ethyl acetate=8:1) is used, and as a result, 3 g of colorless oil is obtained, the yield is 89%, and the said obtained is used directly in the following reaction step.

(8) Preparation of 3,3a,4,5-tetrahydro-3,3-dimethyl-1-(3-methyl-2-butenyl)-10-methoxy methyleneoxy-1,5-dimethylene-1H,7H-furan[3,4-d]xanthene-7,13-diketone In preparation of 3,3a,4,5-tetrahydro-3,3-dimethyl-1-(3-methyl-2-butenyl)-10-methoxy methyleneoxy-1,5-dimethylene-1H,7H-furan[3,4-d]xanthene-7,13-diketone, 3 g of 2-methoxy methyleneoxy-5,6-methyl butenyl-9H-xanthenone is dissolved in 30 mL of DMF, the said mixture reacts at 125° C. for 6 hours, and the solvent is evaporated. The obtained residue is separated and purified with the aid of column chromatography, and as a result, 1.4 g of white solid is obtained, and the yield is 45%; m.p. is 168° C.-169° C.; 1H-NMR (300 MHz, CDCl3): 0.92 (s, 3H), 1.17-1.29 (m, 7H), 1.63 (s, 3H), 2.24 (dd, J1=13.5 Hz, J2=4.5 Hz, 1H), 2.37 (d, J=9.6, 1H), 2.51 (d, J=9.3 Hz, 2H), 3.36-3.44 (m, 4H), 4.36 (m, 1H), 5.15 (s, 2H), 6.57 (d, J=2.1 Hz, 1H), 6.64 (dd, J1=8.7 Hz, J2=2.1 Hz, 1H), 7.31 (d, J=6.9 Hz, 1H), 7.80 (d, J=8.7 Hz, 1H); IR (KBr): 2974.4, 2909.6, 1737.2, 1647.4, 1611.2, 1499.2, 1438.5, 1290.5, 1150.5, 1079.2, 1009.2, 982.4; EI-MS (m/z): 424, 396, 381, 368, 353, 327, 299, 285, 257; Anal. Calcd for C25H28O6(%): C, 70.74; H, 6.65. Found: C, 70.64; H, 6.95.

(9) Preparation of 3,3a,4,5-tetrahydro-3,3-dimethyl-1-(3-methyl-2-butenyl)-10-hydroxy-1,5-dimethylene-1H,7H-furan[3,4-d]xanthene-7,13-diketone In preparation of 3,3a,4,5-tetrahydro-3,3-dimethyl-1-(3-methyl-2-butenyl)-10-hydroxy-1,5-dimethylene-1H,7H-furan[3,4-d]xanthene-7,13-diketone, 1.4 g of 3,3a,4,5-tetrahydro-3,3-dimethyl-1-(3-methyl-2-butenyl)-10-methoxy methyleneoxy-1,5-dimethylene-1H,7H-furan[3,4-d]xanthenoid-7,13-diketone is dissolved in 18 mL of mixed solution containing dichloromethane and ethyl ether (dichloromethane: ethyl ether=1:1), the said mixture is cooled in an ice-bath, 10 mL of concentrated HCl is added, and the said mixture reacts at room temperature for 1 hour. After the reaction, the said reaction solution is extracted with ethyl acetate, and washed with saturated NaCl solution. The ethyl ester phase is dried and condensed, and then separated and purified with the aid of column chromatography, the eluent (petroleum ether/ethyl acetate=4:1) is used, and as a result, 686 mg of yellow solid is obtained, and the yield is 50%; m.p. is 197° C.-199° C.; 1H-NMR (300 MHz, DMSO): 1.02 (s, 3H), 1.22-1.33 (m, 7H), 1.68 (s, 3H), 2.31 (dd, J1=13.5 Hz, J2=3.9 Hz, 1H), 2.42-2.57 (m, 3H), 3.49 (d, J=6.6 Hz, 1H), 4.4 (m, 1H), 6.46 (s, 1H), 6.63 (d, J=9 Hz, 1H), 7.37 (d, J=6.9 Hz, 1H), 7.46 (d, J=9, 1H); IR (KBr): 3376, 3275.5, 2970.6, 2927.1, 1738, 1650, 1607, 1584, 1493, 1332, 1278, 1233.5, 1146, 958, 866, 745; EI-MS (m/z): 379 ([M−H]+); Anal. Calcd for $C_{23}H_{24}O_5$(%): C, 72.61%; H, 6.36%. Found: C, 72.29%; H, 6.54%.

Example 5

The following formula represents a 3,3a,4,5-tetrahydro-3,3-dimethyl-1-(3-hydroxymethyl-2-butenyl)-10-hydroxyl-1,5-dimethylene-1H,7H-furan[3,4-d]xanthene-7,13-diketone endocyclic compound:

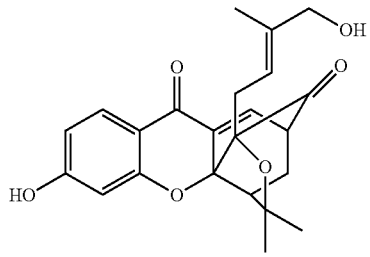 [SMILES: C/C(=C\CC12OC(C)(C)C3CC(C=C4C(=O)c5ccc(O)cc5OC431)C2=O)CO]

The 3,3a,4,5-tetrahydro-3,3-dimethyl-1-(3-methyl-2-butenyl)-10-hydroxyl-1,5-dimethylene-1H,7H-furan[3,4-d] xanthene-7,13-diketone compound is used as a starting material, the operating procedures are the same as those described in Example 3, and as a result, 746 mg of yellow solid is obtained, and the total yield is 4%.

Example 6

The following formula represents a 3,3a,4,5-tetrahydro-3,3-dimethyl-1-(3-methyl-2-butenyl)-9-hydroxyl-1,5-dimethylene-1H,7H-furan[3,4-d]xanthene-7,13-diketone endocyclic compound (CPUY I-3).

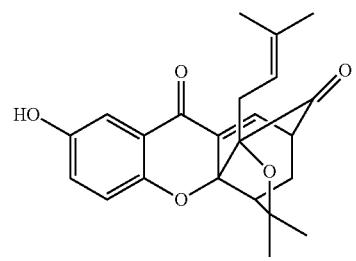 [SMILES: CC(C)=CCC12OC(C)(C)C3CC(C=C4C(=O)c5cc(O)ccc5OC431)C2=O]

Similar to Example 4, except that the compound 2,5-dimethyoxy benzoicacid is used instead of 2,4-dimethoxy benzoicacid, and as a result, 690 mg of yellow solid is obtained, and the yield is 3.3%; m.p. is 158° C.-159° C.; 1H-NMR (300 MHz, CDCl₃): 0.91 (s, 3H), 1.18-1.31 (m, 7H), 1.65 (s, 3H), 2.27 (dd, J1=13.5 Hz, J2=4.5 Hz, 1H), 2.46 (d, J=9.6, 1H), 2.62 (d, J=9.3, 2H), 3.52 (t, J=4.5 Hz, 1H), 4.34 (m, 1H), 6.04 (s, 1H), 6.91 (d, J=9 Hz, 1H), 7.06 (dd, J1=9 Hz, J2=3 Hz, 1H), 7.35 (d, J=6.9 Hz, 1H), 7.41 (d, J=3 Hz, 1H), EI-MS (m/z): 380 [M+], 352, 337, 283, 255, 213; Anal. Calcd for $C_{23}H_{24}O_5$(%): C, 72.61%; H, 6.36%. Found: C, 72.33%; H, 6.50%.

Example 7

The following formula represents a 3,3a,4,5-tetrahydro-3,3-dimethyl-1-(3-hydroxymethoxy-2-butenyl)-9-hydroxyl-1,5-dimethylene-1H,7H-furan[3,4-d]xanthene-7,13-diketone endocyclic compound.

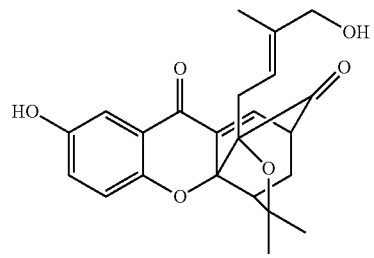 [SMILES: C/C(=C\CC12OC(C)(C)C3CC(C=C4C(=O)c5cc(O)ccc5OC431)C2=O)CO]

The 3,3a,4,5-tetrahydro-3,3-dimethyl-1-(3-methyl-2-butenyl)-9-hydroxyl-1,5-dimethylene-1H,7H-furan[3,4-d] xanthene-7,13-diketone endocyclic compound is used as starting material, the rest of the procedures are the same as those described in Example 3, and as a result, 753 mg of yellow solid is obtained, and the total yield is 4%.

Example 8

The following formula represents a 3,3a,4,5-tetrahydro-3,3-dimethyl-1-(3-methyl-2-butenyl)-11-hydroxyl-1,5-dimethylene-1H,7H-furan[3,4-d]xanthene-7,13-diketone endocyclic compound (CPUY I-4).

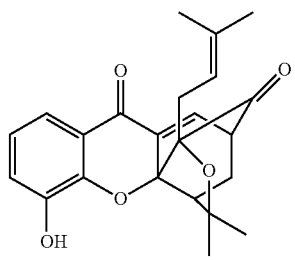 [SMILES: CC(C)=CCC12OC(C)(C)C3CC(C=C4C(=O)c5cccc(O)c5OC431)C2=O]

Similar to Example 4, except that the compound 2,3-dimethoxy benzoic acid is used as a starting material instead of 2,4-dimethoxy benzoic acid, and as a result, 820 mg of yellow solid is obtained, and the yield is 5%; m.p. is 203° C.-205° C.; 1H NMR (300 MHz, DMSO): 0.82 (s, 3H), 1.19-1.34 (m, 7H), 1.64 (s, 3H), 2.27 (dd, J1=13.5 Hz, J2=4.5 Hz, 1H), 2.46-2.56 (m, 3H), 3.45 (m, 1H), 4.45 (m, 1H), 5.38 (s, 1H), 6.90 (t, J=8.1 Hz, 1H), 7.11 (dd, J1=7.8 Hz, J1=1.2 Hz, 1H), 7.43 (d, 1H), 7.46 (d, J=9 Hz, 1H); IR (KBr): 3425, 2966.2, 2925.1, 1738.22, 1650, 1607, 1583, 1493, 1377, 1279, 1233.9, 1152, 748.9; EI-MS (m/z): 380, 352, 337, 309, 283, 255, 241, 213; Anal. Calcd for C23H24O5(%): C, 72.61%; H, 6.36%. Found: C, 72.60%; H, 6.70%.

Example 9

The following formula represents a 3,3a,4,5-tetrahydro-3,3-dimethyl-1-(3-hydroxymethoxy-2-butenyl)-11-hydroxyl-1,5-dimethylene-1H,7H-furan[3,4-d]xanthene-7,13-diketone endocyclic compound.

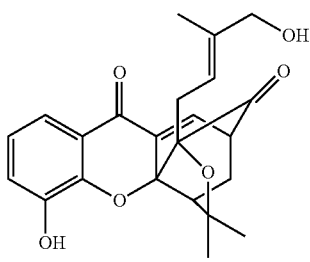 [SMILES: C/C(=C\CC12OC(C)(C)C3CC(C=C4C(=O)c5cccc(O)c5OC431)C2=O)CO]

The 3,3a,4,5-tetrahydro-3,3-dimethyl-1-(3-methyl-2-butenyl)-11-hydroxyl-1,5-dimethylene-1H,7H-furan[3,4-d] xanthene-7,13-diketone endocyclic compound is used as a starting material, the rest of procedures are same as those described in Example 3, and as a result, 755 mg of yellow solid is obtained, and the yield is 4%.

Example 10

The following formula represents a 3,3a,4,5-tetrahydro-3,3-dimethyl-1,11-bis(3-methyl-2-butenyl)-10-hydroxyl-1,5-dimethylene-1H,7H-furan[3,4-d]xanthene-7,13-diketone endocyclic compound (CPUY I-5).

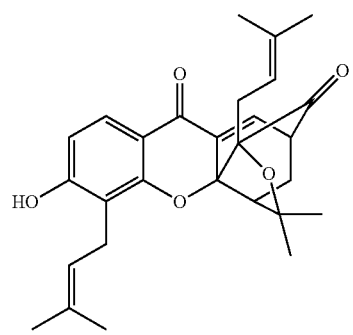 [SMILES: CC(C)=CCc1c(O)ccc2c1OC13C(=CC4CC1C(C)(C)OC3(CC=C(C)C)C4=O)C2=O]

(Step 1) Preparation of 3,4,6-trimethyl butynyl-9H-xanthenone

In preparation of 3,4,6-trimethyl butynyl-9H-xanthenone, 2.7 g (11.07 mmol) of 3,4,6-trimethyl-9H-xanthenone is dissolved in 100 mL of acetone; subsequently, 7.34 g (44.18 mmol, 4 equiv) of KI, 6.1 g (44.28 mmol, 4 equiv) of K₂CO₃ and 0.21 g (0.8 mmol, 0.1 equiv) of CuI are added in turn; the said mixture is stirred at room temperature for 15 min; 7.29 ml (66.42 mmol, 6 equiv) chloro-methyl butyne is added; and the said mixture reacts at 50° C. for 6 hours. The reaction solution is vacuum filtered and the filtrate is condensed. The resulting residue is separated and purified with the aid of column chromatography, the eluent (petroleum ether/ethyl acetate=8:1) is used, and as a result, 2.4 g of orange solid is obtained, and the yield is 49%; m.p. is 117° C.-119° C., ¹H NMR (300 MHz, CDCl₃): δ 1.76 (s, 12H), 1.82 (s, 6H), 2.33 (s, 1H), 2.65 (s, 1H), 2.69 (s, 1H), 7.16 (dd, J1=8.7 Hz, J1=2.1 Hz, 1H), 7.40 (d, J=2.1 Hz, 1H), 7.62 (d, J=9.0 Hz, 1H), 8.04 (d, J=9.0 Hz, 1H), 8.22 (d, J=8.7 Hz, 1H), EI-MS (m/z): 442, 427, 376, 361, 324, 310, 281, 244.

(Step 2) Preparation of 3,4,6-trimethyl butenyl-9H-xanthenone

In preparation of 3,4,6-trimethyl butenyl-9H-xanthenone, 200 mg of 2,5,6-trimethyl butynyl-9H-xanthenone (22) and (0.45 mmol) of xanthenone are dissolved in 30 mL of ethanol, 20 mg of 10% Pd/BaSO₄ is added, and the said mixture reacts at room temperature for 4 hours. The obtained reaction solution is vacuum filtered and the filtrate is condensed. The resulting residue is separated and purified with the aid of column chromatography, the eluent (petroleum ether/ethyl acetate=8:1) is used, and as a result, 170 mg of light green oil is obtained, and the yield is 85%; 1H NMR (300 MHz, CDCl₃): 1.56 (s, 12H), 1.60 (s, 6H), 5.16~5.28 (m, 6H), 6.11~6.34 (m, 3H), 6.95 (dd, J1=9 Hz, J2=2.1 Hz, 1H), 7.05~7.10 (m, 2H), 7.89 (d, J=9 Hz, 1H), 8.14 (d, J=9.0 Hz, 1H), EI-MS (m/z): 448, 436, 420, 405, 380, 365, 325, 312, 256, 244.

(3) Preparation of 3,3a,4,5-tetrahydro-3,3-dimethyl-1,11-bis(3-methyl-2-butenyl)-10-hydroxyl-1,5-dimethylene-1H,7H-furan[3,4-d]xanthene-7,13-diketone In preparation of 3,3a,4,5-tetrahydro-3,3-dimethyl-1,11-bis(3-methyl-2-butenyl)-10-hydroxyl-1,5-dimethylene-1H,7H-furan[3,4-d]xanthene-7,13-diketone, 120 mg of 2,5,6-trimethyl butenyl-9H-xanthenone (23) is dissolved in 120 ml of DMF, the said mixture reacts at 125° C. for 4 hours, and subsequently, the DMF is heated and vacuum evaporated. the resulting residue is separated and purified with the aid of column chromatography, the eluent (petroleum ether/ethyl acetate=4:1) is used, and as a result, 65 mg of yellow solid is obtained, and the yield is 53%. The obtained is crystallized with 95% ethanol, and as a result, the orange fine crystal is obtained, and the m.p. is 158° C.-160° C.; 1H NMR (300 MHz, CDCl$_3$): 0.93 (s, 3H), 1.29-1.33 (m, 7H), 1.71 (s, 3H), 1.77 (s, 3H), 1.83 (s, 3H), 2.33 (dd, J1=13.5 Hz, J2=4.5 Hz, 1H), 2.50 (d, J=9.3, 1H), 2.57 (d, J=8.7 Hz, 2H), 3.46-3.55 (m, 3H), 4.40-4.45 (m, 1H), 5.28 (t, J=6.6 Hz, 1H), 6.30 (s, 1H), 6.58 (d, J=8.7 Hz, 1H), 7.43 (d, J=6.9 Hz, 1H), 7.80 (d, J=8.7 Hz, 1H), IR (KBr): 3438.7, 2964.3, 2922.1, 2849.9, 1738.9, 1649.6, 1605.3, 1433.0, 12984.6, 1262.8, 1079.6, 1046.7, 802, EI-MS (m/z): 448, 420, 405, 377, 351, Anal. calcd for C$_{28}$H$_{32}$O$_5$.H$_2$O (%): C, 72.08; H, 7.35. Found: C, 72.33; H, 7.36.

Example 11

The following formula represents a 3,3a,4,5-tetrahydro-3,3-dimethyl-1,8-bis(3-methyl-2-butenyl)-9-hydroxyl-1,5-dimethylene-1H,7H-furan[3,4-d]xanthene-7,13-diketone endocyclic compound (CPUY I-6).

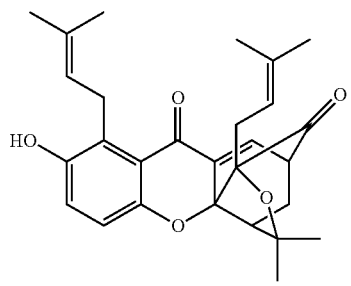 [SMILES: CC(C)=CCc1c(O)ccc2c1C(=O)C1=CC3CC4C(C)(C)OC(CC=C(C)C)(C3=O)C14O2]

Similar to the procedures described in Example 10, except that the compound 2,5,6-hydroxyl-9H-xanthenone is used as a starting material instead of 3,4,6-trimethyl-9H-xanthenone, and as a result, 80 mg of orange solid is obtained, and the yield is 40%; m.p. is 138° C.-139° C.; 1H NMR (300 MHz, CDCl$_3$): δ 1.03 (s, 3H), 1.16-1.23 (m, 4H), 1.32 (s, 3H), 1.63 (s, 3H), 1.67 (s, 3H), 1.77 (s, 3H), 2.22 (dd, J1=13.5 Hz, J2=4.5 Hz, 1H), 2.29 (d, J=9.6, 1H), 2.56 (d, J=8.7 Hz, 2H), 3.38 (dd, J1=6.9 Hz, J2=4.5 Hz, 1H), 3.88 (d, J=6.6, 2H), 4.38 (t, J=8.7 Hz, 1H), 5.13 (t, J=6.6, 1H), 5.39 (s, 1H), 6.81 (d, J=9 Hz, 1H), 7.00 (d, J=9 Hz, 1H), 7.18 (d, J=6.9 Hz, 1H), IR (KBr): 3506.1, 3171.6, 2967.4, 2918.6, 1737.0, 1659.6, 1606.3, 1486.0, 1443.5, 1376.5, 1298.6, 1221.8, 1145.25, 1042.6, 822.7, 790.5, EI-MS (m/z): 448, 420, 378, Anal. calcd for C$_{28}$H$_{32}$O$_5$.H$_2$O (%): C, 72.08; H, 7.35. Found: C, 72.10; H, 7.30.

Example 12

The following formula represents a 1,3a,4,11a-tetrahydro-3,3-dimethyl-1,7-bis(3-methyl-2-butenyl)-8-hydroxyl-3H-1,4-a-dimethylene-10H-furan[3,4-b]xanthene-10,12-diketone endocyclic compound (CPUY I-7).

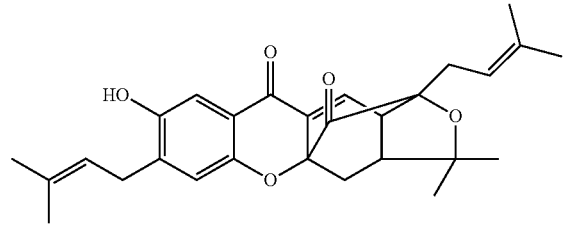 [SMILES: CC(C)=CCc1cc2c(cc1O)C(=O)C1=CC3C4CC1(O2)C(=O)C3(CC=C(C)C)OC4(C)C]

Similar to the procedure described in Example 10, except that the compound 2,5,6-hydroxyl-9H-xanthenone is used as a starting material instead of 3,4,6-trimethyl-9H-xanthenone, and as a result, 40 mg of orange crystals are obtained, and the yield is 20%; m.p. is 148° C.-150° C.; 1H NMR (300 MHz, CDCl$_3$): 1.30 (s, 3H), 1.33 (s, 3H), 1.52 (s, 3H), 1.64 (s, 3H), 1.67 (s, 3H), 1.76 (s, 4H), 2.01 (dd, J1=8.4 Hz, J2=14.7 Hz, 1H), 2.10 (dd, J1=4.5, J1=9.9, 1H), 2.56 (d, J=8.7 Hz, 2H), 3.65 (dd, J1=6.9 Hz, J2=4.5 Hz, 1H), 3.82 (d, J=6.6, 2H), 4.95 (t, J1=6.9 Hz, J2=8.1 Hz, 1H), 5.11 (m, 2H), 6.96 (s, 2H), 7.00 (d, J=6.9 Hz, 1H), IR (KBr): 3506.1, 3171.6, 2967.4, 2918.6, 1737.0, 1659.6, 1606.3, 1486.0, 1443.5, 1376.5, 1298.6, 1221.8, 1145.25, 1042.6, 822.7, 790.5, ESI-MS (m/z): 447 ([M+H]$^+$), Anal. calcd for C$_{28}$H$_{32}$O$_5$.H$_2$O (%): C, 72.08; H, 7.35. Found: C, 72.11; H, 7.40.

Example 13

The following formula represents a 3,3a,4,5-tetrahydro-3,3-dimethyl-1,10-bis(3-methyl-2-butenyl)-11-hydroxyl-1,5-dimeth ylene-1H,7H-furan[3,4-d]xanthene-7,13-diketone endocyclic compound (CPUY I-8).

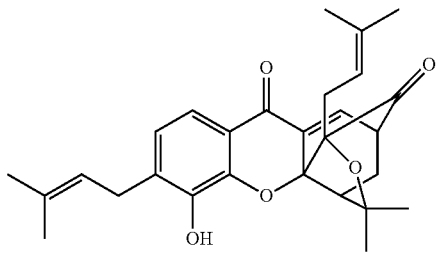 [SMILES: CC(C)=CCc1ccc2c(c1O)OC13C(=CC4CC1C(C)(C)OC3(CC=C(C)C)C4=O)C2=O]

Similar to the procedure described in Example 10, except that the compound 3,4,5-trihydroxyl-9H-xanthenone is used as starting a material instead of 3,4,6-trimethyl-9H-xanthenone, and as a result, 60 mg of yellow solid is obtained, and the yield is 40%; m.p. is 157° C.-158° C.; 1H NMR (300 MHz, CDCl$_3$): 0.81 (s, 3H), 1.24-1.29 (m, 7H), 1.64 (s, 3H), 1.67 (s, 3H), 1.68 (s, 3H), 2.27 (dd, J1=13.5 Hz, J2=4.8 Hz, 1H), 2.45-2.49 (m, 3H), 3.33 (d, J=7.2 Hz, 2H), 3.43 (dd, J1=6.6 Hz, J2=4.8 Hz, 1H), 4.47 (t, J=6.6 Hz, 1H), 5.20 (dd, J1=7.2 Hz, J2=1.2 Hz, 1H), 5.41 (s, 1H), 6.79 (d, J=8.1 Hz, 1H), 7.37 (d, J=8.1 Hz, 1H), 7.41 (d, J=6.6 Hz, 1H), IR (KBr): 3416.4, 2969.4, 2909.6, 1739.5, 1654.8, 1607.8, 1448, 1313.7, 1249.2, 1213.7, 1037.7, EI-MS (m/z): 448, 436, 420, 405, 377, 351, 323, 281, Anal. calcd for C28H32O5.CH3OH (%): C, 72.08; H, 7.35. Found: C, 72.02; H, 7.30.

What is claimed is:

1. A compound of Formula (I) or its pharmaceutically acceptable salt:

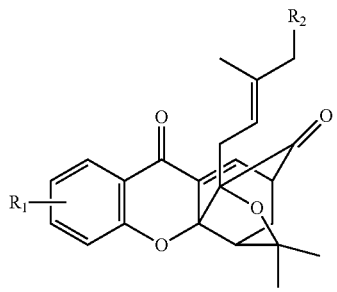

Formula (I)

wherein $R_1$ is a single substituent or a multi substituent group; when $R_1$ is the single substituent group, $R_1$ is a hydroxyl group; and when $R_1$ is the multi substituent group, one of the substituent groups is a hydroxyl group, and the rest of the substituent groups are selected from an amino group, a nitro group, a cyano group, an alkyl group containing $C_1$-$C_6$ carbons, or an alkenyl group containing $C_2$-$C_6$ carbons;

wherein $R_2$ is halogen, a hydroxyl group, an alkoxy group containing $C_1$-$C_4$ carbons, an amide group containing $C_1$-$C_4$ carbons, a carboxyl group, or an aldehyde group.

2. The compound of Formula (I) or its pharmaceutically acceptable salt according to claim 1, wherein $R_1$ is a single substituent hydroxyl group.

3. The compound of Formula (I) or its pharmaceutically acceptable salt according to claim 1, wherein $R_1$ is a double substituent group, wherein one of the substituent groups is a hydroxyl group, and the other substituent group is an isopentene group.

4. The compound of Formula (I) or its pharmaceutically acceptable salt according to claim 1, wherein $R_2$ is a hydroxyl group, an aldehyde group, or a carboxyl group.

5. A method for preparing the compound of claim 1 wherein $R_2$ is a hydroxyl group, the method comprising:

preparing compound 9 from compound 4 under reaction condition a:

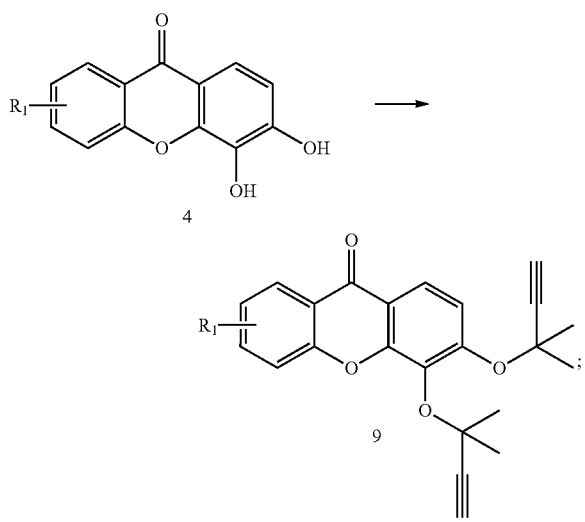

preparing compound 10 from compound 9 under reaction condition b:

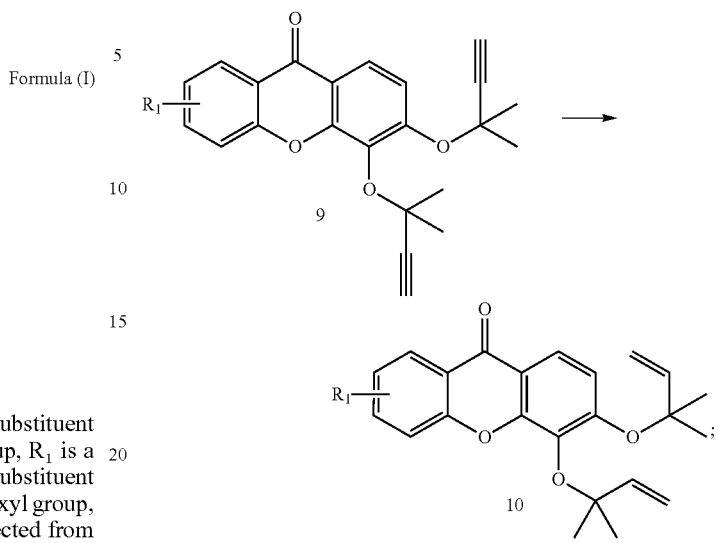

preparing compound 11 from compound 10 under reaction condition c:

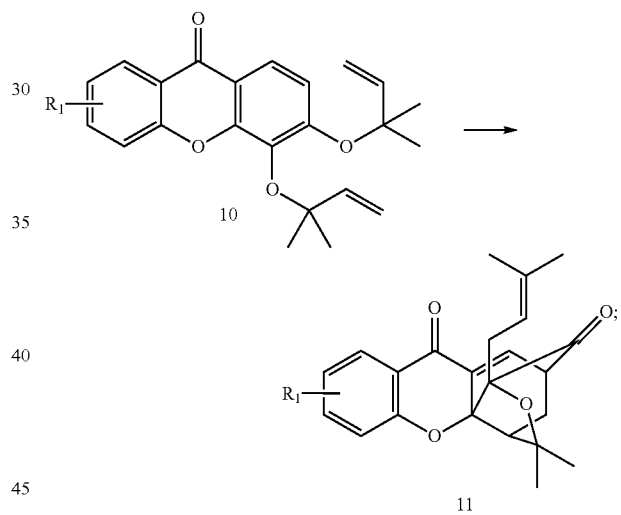

and preparing the compound of Formula (I) from compound 11 under reaction condition d;

wherein $R_1$ is the same as in claim 1; a, b and c are reaction conditions:

a is $K_2CO_3$, KI, chloro-methyl-butyne, CuI and acetone;

b is 10% $Pd/BaSO_4$ and ethyl acetate;

c is N,N-dimethyl formamide; and d is oxidation.

6. A pharmaceutical composition, comprising the compound of Formula (I) or its pharmaceutically acceptable salt according to claim 1 and pharmaceutically acceptable carrier thereof.

7. A method of treating breast cancer or gastric carcinoma, comprising:

administering the compound of Formula (I) or its pharmaceutically acceptable salt according to claim 1.

* * * * *